United States Patent
Wieselblad

(10) Patent No.: US 9,358,343 B2
(45) Date of Patent: Jun. 7, 2016

(54) MEDICAMENT DELIVERY DEVICE

(71) Applicant: Carebay Europe Ltd, Swatar (MT)

(72) Inventor: Anders Wieselblad, Stockholm (SE)

(73) Assignee: Carebay Europe Ltd, Sliema (MT)

( * ) Notice: Subject to any disclaimer, the term of this patent is extended or adjusted under 35 U.S.C. 154(b) by 0 days.

(21) Appl. No.: 14/395,001

(22) PCT Filed: Apr. 9, 2013

(86) PCT No.: PCT/EP2013/057376
§ 371 (c)(1),
(2) Date: Oct. 16, 2014

(87) PCT Pub. No.: WO2013/156345
PCT Pub. Date: Oct. 24, 2013

(65) Prior Publication Data
US 2015/0080811 A1     Mar. 19, 2015

Related U.S. Application Data

(60) Provisional application No. 61/625,159, filed on Apr. 17, 2012.

(30) Foreign Application Priority Data

Apr. 17, 2012    (SE) ...................................... 1250382

(51) Int. Cl.
*A61M 5/315*    (2006.01)

(52) U.S. Cl.
CPC ......... *A61M 5/31551* (2013.01); *A61M 5/3155* (2013.01); *A61M 5/31541* (2013.01); *A61M 5/31578* (2013.01); *A61M 5/31585* (2013.01); *A61M 5/31593* (2013.01)

(58) Field of Classification Search
CPC .................... A61M 5/31551; A61M 5/31541; A61M 5/31593; A61M 5/31578; A61M 5/31585; A61M 5/3155; A61M 5/31565; A61M 5/31576
USPC ...................................... 604/207, 228, 68–72
See application file for complete search history.

(56) References Cited

PUBLICATIONS

Veasy et al., WO 2004/078242, date: Sep. 19, 2004.*
Moller, WO 01/95959, date: Dec. 20, 2001.*
Moller et al., EP 1645301A1, date: Dec. 4, 2006.*
Sams, WO 2008/053243A2, date: May 8, 2008.*

* cited by examiner

*Primary Examiner* — Manuel Mendez
(74) *Attorney, Agent, or Firm* — Piedmont Intellectual Property

(57) ABSTRACT

A medicament delivery device includes a housing having proximal and distal ends; a hollow piston plunger within the housing; a telescopic dose drum concentric between the housing and the plunger; and a plunger driver to drive the plunger toward the proximal end having a hollow drive drum sleeve movable within and coupleable to the piston plunger and fixed to the dose drum; an actuator operably connected to the drive drum sleeve; and a stop body for inhibiting rotation of the dose drum and drive drum sleeve when a set dose equals a remaining dose in a medicament container. The drive drum sleeve and piston plunger are operatively coupled such that axial movement of the actuator toward the proximal end forces the drive drum sleeve and piston plunger to couple, whereby the piston plunger and dose drum are displaced toward the proximal end for delivering the set dose.

12 Claims, 10 Drawing Sheets

MEDICAMENT DELIVERY DEVICE

This application is a national-phase entry under 35 U.S.C. §371 of International Application PCT/EP2013/057376.

TECHNICAL FIELD

The present invention relates to a medicament delivery device and in particular a device capable of delivering a dose of medicament set by user before delivery.

BACKGROUND

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a delivery member attached to the opposite end of the compartment, such as, e.g., a needle, a nozzle or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors. In this context, the so called pen-injectors are becoming quite common, where the injection is performed by manually pushing at a distal end of the device. With this type of injector there has also been a development regarding delivering different dose quantities with the same device, i.e. to be able to set a certain prescribed dose before delivery.

A number of such devices have been developed, such as the device disclosed in EP-A-1 601 395. Here the device is arranged with a dose setting drum that can be rotated in relation to a housing and a drive sleeve that, upon manual operation by a user, drives a plunger rod to deliver a set dose of medicament. In order to provide the function of setting a dose with the dose setting drum and delivering a dose with the drive sleeve, there has to be some sort of connection/disconnection mechanism between them. Thereby a clutch or unidirectional connection mechanism has been developed for providing the desired function. This solution entails a number of components that are to interact with each other as well as a number of threaded engagement and connection mechanisms that require careful design in order for the manually applied force by a user not to be too large, or the device otherwise will not function properly. There is also a question whether the solution according to EP-A-1 601 395 can provide the possibility of resetting a set dose in a simple and efficient manner.

Another feature with the device of EP-A-1 601 395 is that the setting of a dose larger than the remaining quantity should be prevented in that when a nut reaches the end of a helical thread of the connection mechanism, the nut stops rotating of a dose dial sleeve and the drive sleeve will thus become locked together preventing rotation of the dose dial sleeve and setting of a larger dose. This direct action between threads is not so precise in that there is no distinct stop between the components. Rather, the components could be turned in relation to each other quite a turning distance before the friction becomes so high that it is difficult to turn them relative each other any longer. Thus, a user could then erroneously believe that he/she is receiving a larger dose than the actual dose received.

Further, the components, such as the dose setting drum and the drive sleeve as well as the plunger rod are elongated and positioned inside each other. In order to not risk a jamming between the components, a certain play is necessary. Then, such play and gaps between components increase the risk of lack of support and therefore rattling and other noises that may negatively affect a potential user.

SUMMARY

An object of the present invention is to provide a medicament delivery device wherein the drawbacks of the state of the art devices are remedied.

In order to overcome one or several of the above-mentioned problems, a medicament delivery device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site. Further, the term "longitudinal", with or without "axis", refers to a direction or an axis through the device or components thereof in the direction of the longest extension of the device or the component. In a similar manner, the term "transversal", with or without "axis", refers to a direction or an axis through the device or components thereof in a direction generally perpendicular to the longitudinal direction. Also, if nothing else is stated, in the following description wherein the mechanical structure of the device and the mechanical interconnection of its components is described, the device is in an initial non-activated or non-operated state.

The invention provides a medicament delivery device having a housing with a proximal end and a distal end. A hollow piston plunger is arranged within the housing. The piston plunger has a longitudinal axis generally corresponding with the longitudinal direction of the medicament delivery device.

The device of the invention comprises a hollow piston plunger being arranged within the housing and a telescopic dose drum being concentrically arranged between the housing and the piston plunger. The telescopic dose drum being bidirectional movable in relation to the housing and in relation to the piston plunger when setting a dose and delivering a dose.

A piston plunger driving means is also arranged in the device for driving the hollow piston plunger towards the proximal end. The piston drive means may comprise a hollow drive drum sleeve that is movably arranged within the hollow piston plunger. It may further be fixedly connected to the telescopic dose drum such that the hollow drive drum sleeve and the hollow piston plunger are coupleable to each other. In this context it is to be understood that the coupling may be of many designs providing the desired function.

Further, the device comprises a resilient spinning element having a longitudinally rod being movable arranged within the hollow drive drum sleeve, wherein the longitudinally rod and the hollow drive drum sleeve are releasably coupleable to each other; such that after a dose is set, axial movement of the resilient spinning element towards the proximal end forces the longitudinally rod and the hollow drive drum sleeve to couple together and thereby the hollow drive drum sleeve and the hollow piston plunger also to couple together whereby the hollow piston plunger and the telescopic dose drum are displaced towards the proximal end for delivering the set dose, and such that after a set dose is delivered, axial movement of the resilient spinning element towards the distal end forces the longitudinally rod and the hollow drive drum sleeve to decouple and thereby the hollow drive drum sleeve and the hollow piston plunger also to decouple for setting a new dose.

According to preferable feature of the invention, the device further comprises a stop body being connected to the hollow piston plunger such that said stop member is rotatable but not slidable in relation to said hollow piston plunger, and being also connected to the telescopic dose drum such that said stop member is slidable but not rotatable in relation to said telescopic dose. With this solution it is not possible to set a dose that is larger than the remaining quantity in the medicament container. In this manner, the user is alerted that the dose that is to be delivered is smaller than the prescribed dose. Preferably also the quantity of the last dose is indicated to the user such that he or she may have a complementary dose delivery with the missing quantity when the medicament container has been replaced with a new or that the user takes another medicament delivery device.

According to one preferable solution, said stop body is configured to interact with a stop member on said telescopic dose drum when the set dose equals the remaining dose in the medicament container such that rotation of the telescopic dose drum is inhibited. In that context, said stop body is a generally ring-shaped body comprising at least one protrusion, rib or ledge on its outer surface and the telescopic dose drum comprises a first, distal, part and a second, proximal, part being slidably arranged relative to each other wherein said second, proximal, part is a tube shaped body comprising at least one longitudinally extending groove on in its inner surface and wherein said stop member is an end surface of said at least one groove. With this design a purely mechanical stop mechanism is obtained. Also, when a ring-shaped member is used, which is rotatable, a radial support for the piston plunger is also obtained, thereby minimizing the play between components and still minimizing friction between them.

Further a dose setting knob may be arranged, the dose setting knob configured to be grasped by a user for setting a dose when being rotated in a first direction. The dose setting knob may preferably be arranged at a distal area of the device, for easy access.

Further, the dose setting knob may preferably be a separate component connected with the first part of the dose drum at its distal end. As an alternative, the dose setting knob may be integral with the first part, whereby the first part of the telescopic dose drum is configured to rotationally move distally in the first direction relative to the housing during dose setting by the dose setting knob.

As a further alternative, the dose setting knob may be a separate component connected with the drive drum sleeve at its distal end. As another alternative, the dose setting knob is integral with the drive drum sleeve, whereby the drive drum sleeve is configured to rotationally move distally in the first direction relative to the housing during dose setting by the dose setting knob.

Furthermore, the device may comprise an unidirectional means for preventing movement of the piston plunger in the distal direction during setting a dose.

The medicament delivery device may be an injection device, preferably a pen injector.

Other aspects, features, and advantages will be apparent from the summary above, as well as from the description that follows, including the figures and the claims.

BRIEF DESCRIPTION OF THE DRAWINGS

The figures below disclose an embodiment of the invention for illustrational purposes only. In particular, the disclosure within the figures is not meant to limit the range of protection of the invention. The embodiment shown may be modified in many ways within the scope of the claims.

DETAILED DESCRIPTION

Mechanical Structure of an Embodiment

Figure 1:
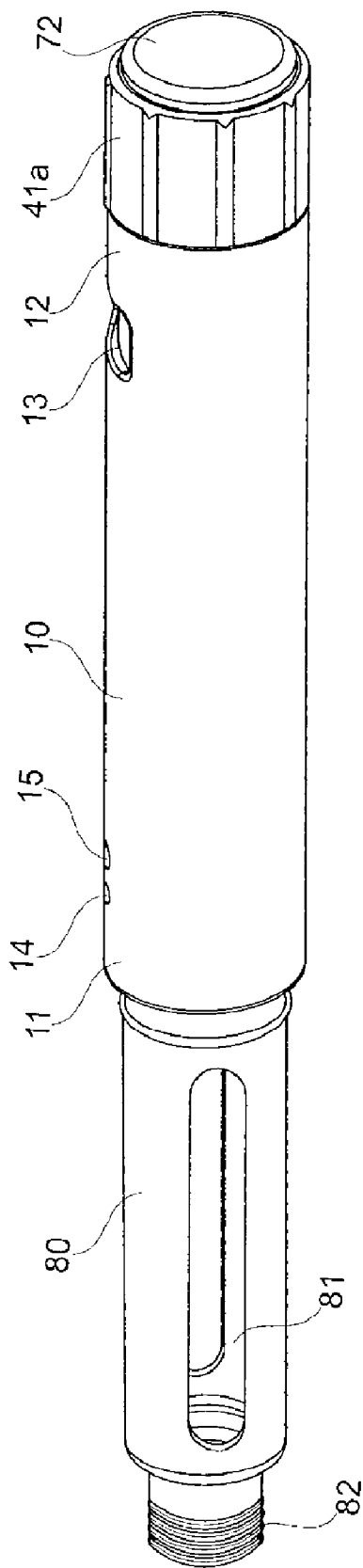
FIG. 1 shows a perspective view of a medicament delivery device according to a preferred embodiment of the invention, shown in the initial state.

FIG. 1 shows a perspective view of a medicament delivery device according to a preferred embodiment of the invention. The medicament delivery device has a proximal end and a distal end and comprises a housing 10 having a proximal part or end 11 and a distal part or end 12. In the assembled state of the medicament delivery device, the housing 10 forms part of the outer surface or appearance of the medicament delivery device. It is however to be understood that the housing may be designed in many other ways.

The medicament delivery device further comprises a medicament container holder 80 which accommodates a medicament container. The medicament container holder 80 also forms part of the outer surface or appearance of the medicament delivery device. The proximal part of the container holder 80 is further arranged with a neck 82 at its proximal end for attaching a per se known and conventional injection needle (not shown). It is however to be understood that other types of connection members, such as bayonet fitting luerlock fittings and the like may be arranged. Also, the medicament container may have an injection needle integrated in its body whereby the neck portion 82 may be omitted.

A cap (not shown) may be provided for releasably covering the proximal end of the device, and thereby the proximal end of the medicament container holder 80, when not in use.

The medicament container holder 80 of the medicament delivery device comprises a window 81 that allows the user to view the progress of medicament delivery, i.e. whether the medicament delivery device is still in its initial stage with the medicament not yet being injected, or whether the medicament container is already emptied. Through window 81, the user can see the medicament container accommodated at least in the medicament container holder 80 (the distal part of the medicament container may reach into the proximal part of the housing 10). In a preferred embodiment, two such windows are provided located at opposite sides of the medicament container holder 80.

Furthermore, at the proximal end 12 of the housing 10, a further window 13 is provided that is used to indicate a set dose to a user, as described in more detail below. At the proximal end 12 of housing 10, a dose setting knob 41*a* for dose setting projects distally.

Figure 2:
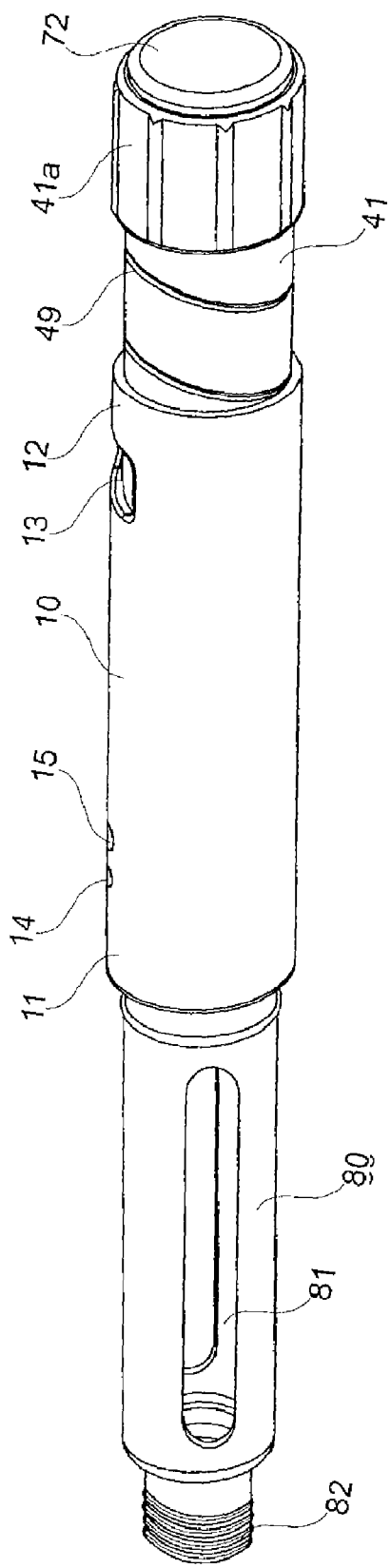
FIG. 2 shows a perspective view of a medicament delivery device according to the preferred embodiment of FIG. 1, shown in the state when a dose is set.

FIG. 1 shows the medicament delivery device in the initial state. When the user grasps the dose setting knob 41*a* and rotates it in a first direction, for example in clockwise direction, the dose setting knob 41*a* and other components move distally, as will be explained in detail below, in order to set a dose. FIG. 2 shows a perspective view of the medicament delivery device in such state, i.e. when a dose is set.

Figure 3:
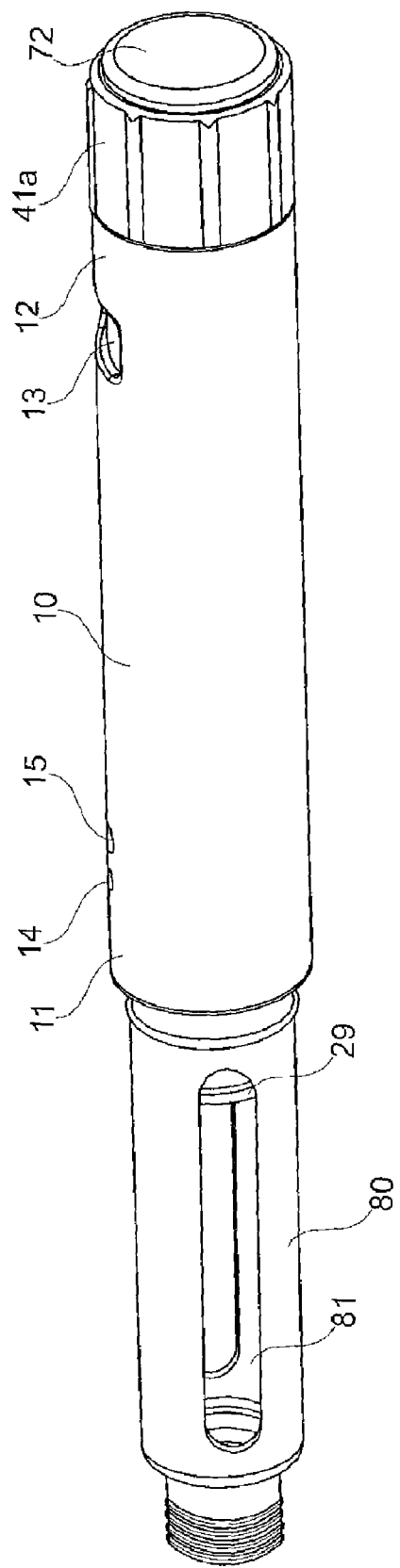
FIG. 3 shows a perspective view of a medicament delivery device according to the preferred embodiment of FIG. 1, shown after a set dose has been delivered.

FIG. 3 shows a perspective view of the medicament delivery device after a set dose has been delivered. As can be seen, the dose setting knob 41*a* and the components linked therewith were moved proximally and the dose setting knob 41*a* is again in its initial position. However, as can be seen at window 81, the piston plunger 20 of the medicament delivery device has been displaced in proximal direction and a stopper 29 within the medicament container can now be seen through the window(s) 81.

Figure 4:
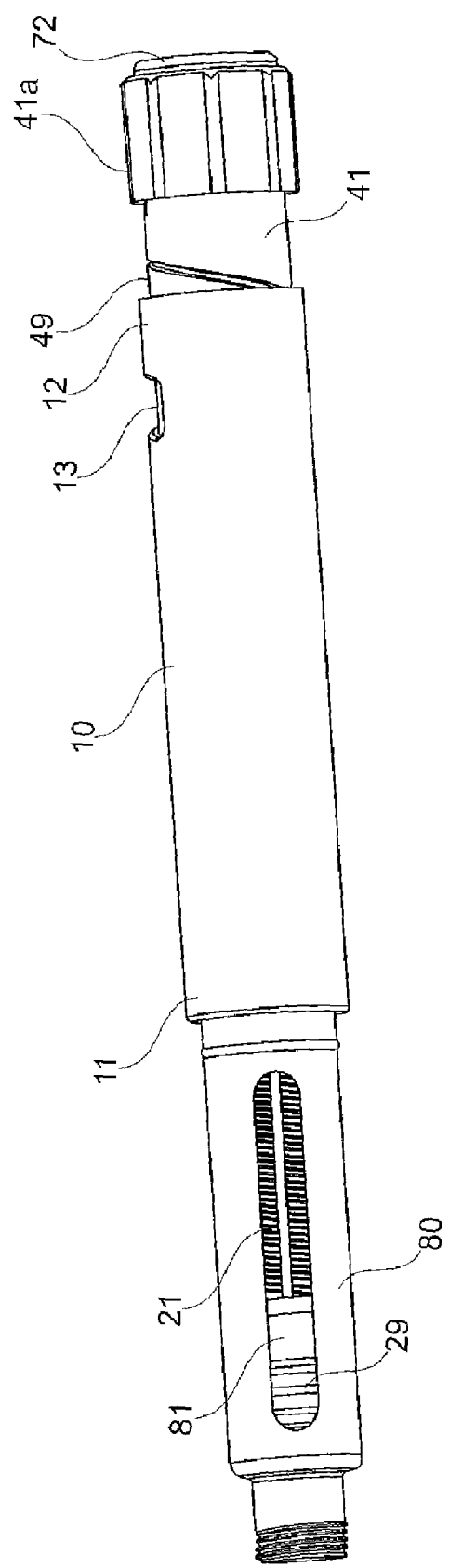
FIG. 4 shows a perspective view of a medicament delivery device according to the preferred embodiment of FIG. 1, shown in a state having all medicament delivered.

FIG. 4 then shows a perspective view of the medicament delivery device in a state having all medicament, i.e. several individual doses delivered. The stopper 29 is now located at the proximal end of the medicament container 85, and part of the piston plunger 20 with its threaded surface 21 can be seen through windows 81.

The medicament container holder 80 is arranged with attachment means for connecting or attaching it to the proximal housing part 11. In the embodiment shown the attachment means comprise a protrusion 83 (see FIG. 5) fitting into a corresponding recess 14. It is however to be understood that other attachment members may be utilized, such as bayonet fittings, threads, or the like for attaching the medicament container holder 80 with the housing 10.

An elongated piston plunger 20 (see FIGS. 5 to 7) is arranged inside the housing 10 and has a longitudinal axis generally corresponding with the longitudinal direction of the medicament delivery device. The piston plunger 20 is arranged with threads 21 (FIG. 6) on at least part of its outer surface. In the preferred embodiment shown in the drawings, a proximal part of the piston plunger 20 comprises a threaded structure 21. On its outer surface, the piston plunger 20 comprises at least one longitudinal groove 25 (FIG. 6) (in the shown embodiment, two such grooves 25 are provided). The proximal end of the piston plunger 20 is arranged with a washer or spinner 28, (FIG. 5) adapted to abut the stopper 29. The stopper 29 is intended to be movably received inside the medicament container 85.

Figure 5:
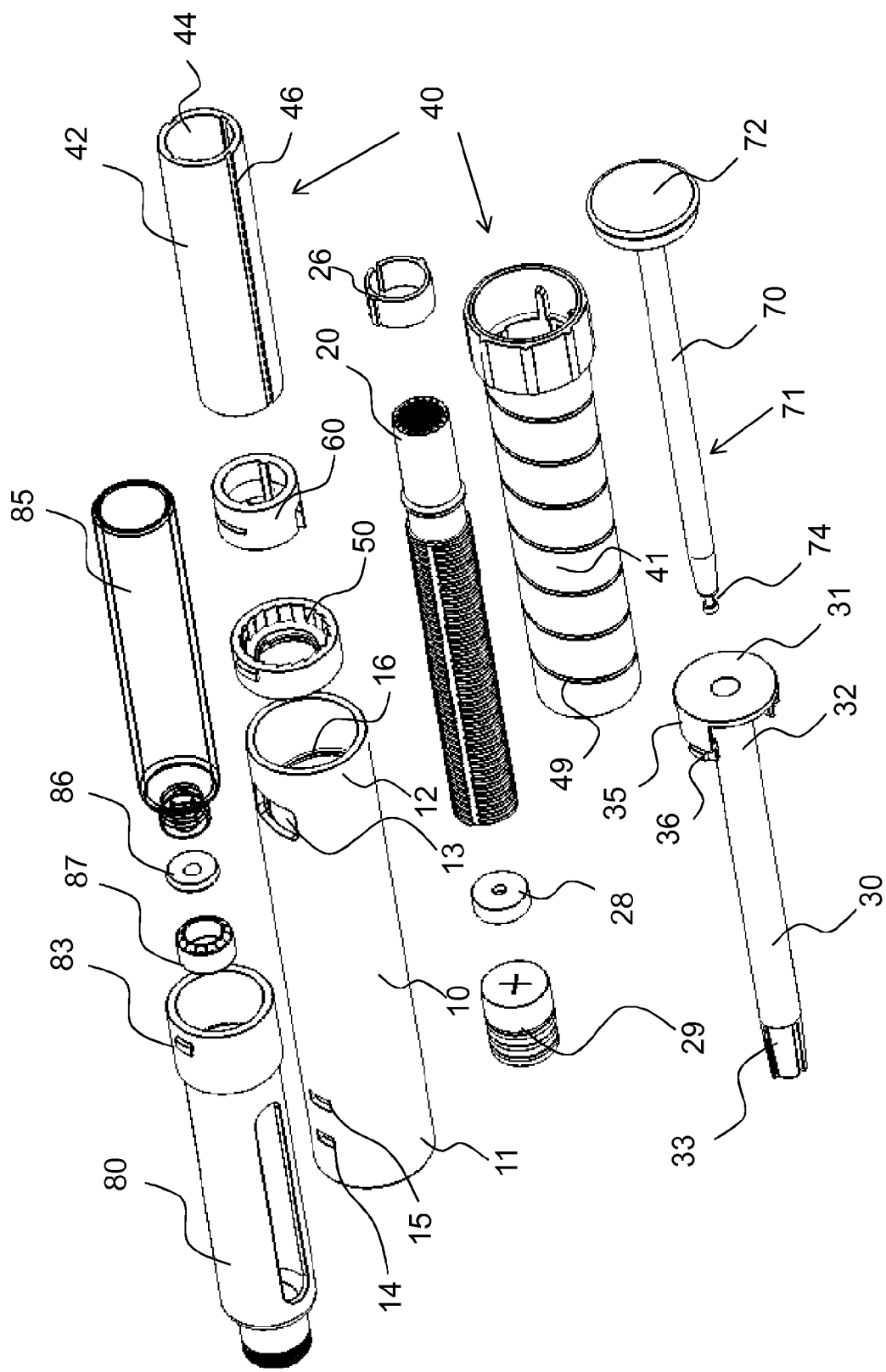
FIG. 5 shows an exploded view of the medicament delivery device according to the preferred embodiment of FIG. 1.

The piston plunger 20 fits into an insert 50 arranged with a central passage 51, (FIG. 7) the center of which generally coincides with the longitudinal axis of the medicament delivery device. The central passage 51 of the thread insert is arranged with threads 52 of complementary design as the threads 21 of the piston plunger 20. The outer surface of the insert 50 comprises at least one protrusion 53 or the like, fitting into corresponding recesses 15 (FIG. 5) on the inner surface of the housing 10, whereby the insert 50 is locked to the proximal housing part 10. As shown in FIG. 5, recess 15 in the housing may be formed as a through hole.

The insert 50 further comprises a central bore 54 at the distal side of the thread insert 50. The diameter of the central bore 54 is larger than the diameter of the central passage 51 so that a stepped configuration is provided. The inner circumferential surface of the central bore 54 is arranged with a circumferentially extending ratchet 55 arranged with sawtooth shaped teeth.

Figure 7:
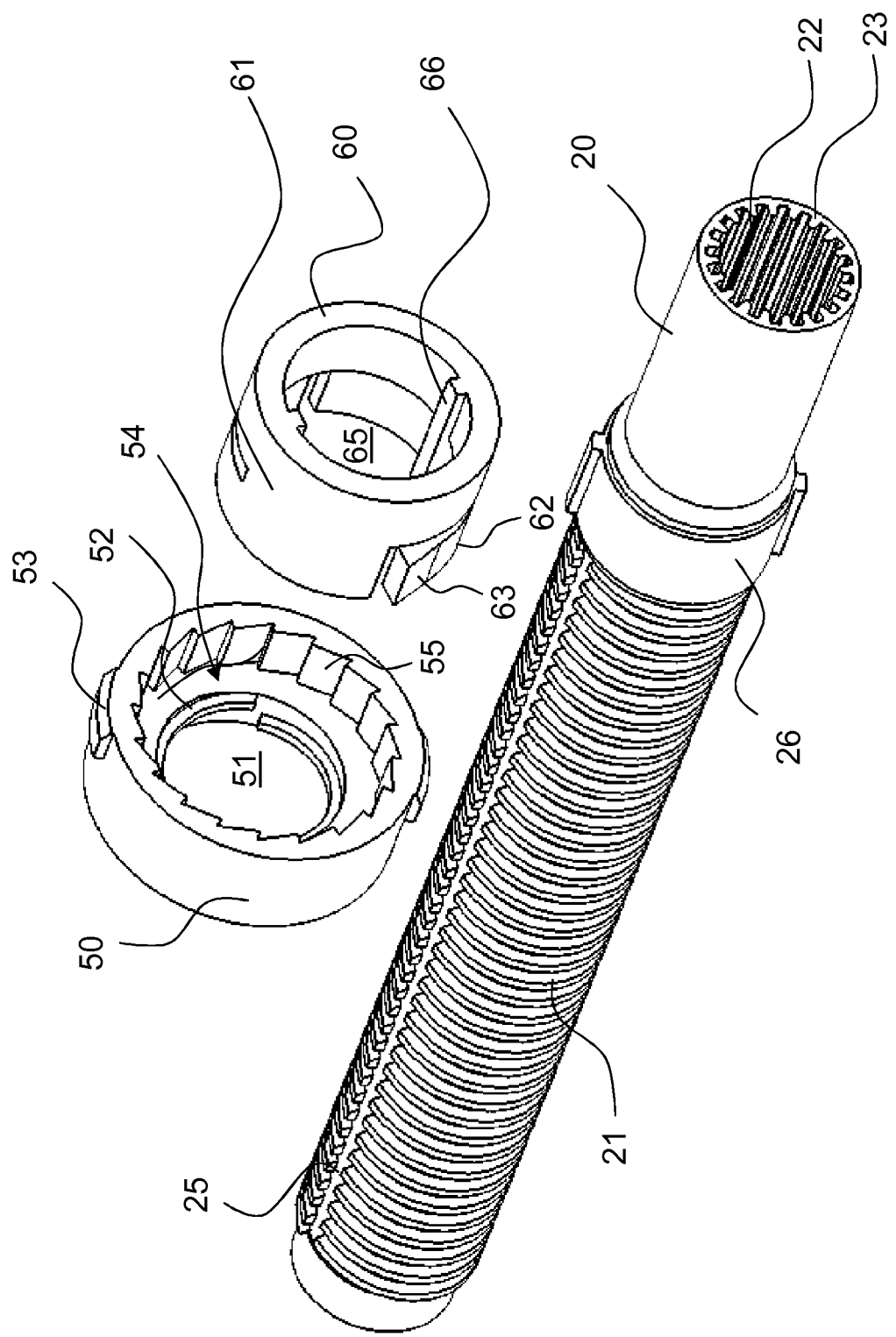
FIG. 7 shows another partly exploded view of the medicament delivery device according to FIG. 1.

The ratchet 55 cooperates with a ring-shaped back rotating blocking element 60 (FIG. 7) which is arranged with two oppositely positioned arms 62, extending on the outer circumferential surface 61 generally in the circumferential direction of the blocking element 60. Although two such arms 62 are shown in FIGS. 5 and 7, a single arm may as well suffice, or more than two arms may be provided, depending on the size of the blocking member 60. The one or more arms 62 are flexible in the generally radial direction. On the outwardly directed surfaces of the arm(s) 62, a ledge 63 is arranged. Each ledge 63 has a shape complementary to the ratchet 55 of the thread insert 50. The back rotating blocking element 60 is further arranged with a central passage 65 (FIG. 7) through which the piston plunger 20 extends. The central passage 65 is arranged with radially inwardly directed protrusions or ribs 66, which protrusions 66 fit into the elongated grooves 25 on the outer surface of the piston plunger 20. This structure provides a rotational lock of the piston plunger 20 but allows a movement of the piston plunger 20 in the longitudinal direction.

The piston plunger 20 is further arranged with a plurality of longitudinal splines or ribs 23 provided on the inner circumferential surface 22 of the hollow piston plunger 20 (FIG. 7). A drive drum sleeve 30 (FIG. 5) of generally tubular shape is arranged radially inside the piston plunger 20. The drive drum sleeve 30 is provided with a distal end wall 31 transversal to the longitudinal axis of the drive drum sleeve 30. The distal end wall 31 has central opening and the drive drum sleeve is hollow in order to receive a resilient spinning element 70 therein, as will be described below. The proximal end of the drive drum sleeve 30 comprises one or more, preferably two, flexible arms 33 extending in the proximal direction. The arms 33 are flexible in that their proximal ends are radially deflectable upon application of a radial force thereon, as will be describe below. The outer surface of each flexible arm 33 comprises a radially projecting piston plunger engagement surface 34 (FIG. 8) for selectively engaging with the longitudinal splines 23 on the inner surface 22 of the piston plunger 25. The shape of the surface 34 may generally correspond to the shape of the circumferentially arranged ribs 23 on the piston plunger 20. The inner surface of each flexible arm 33 comprises a radially engagement protrusion 37 (FIG. 8) for selective engagement with the resilient spinning element 70 located within the hollow drive drum sleeve 30.

The distal end wall 31 forms a coupling element by means of two proximally extending locking arms 35 (FIG. 5). The locking arms 35 comprise at their respective outer surface a locking structure 36 for locking the drive drum sleeve 30 to the inner surface of a dose drum 40.

Figure 6:
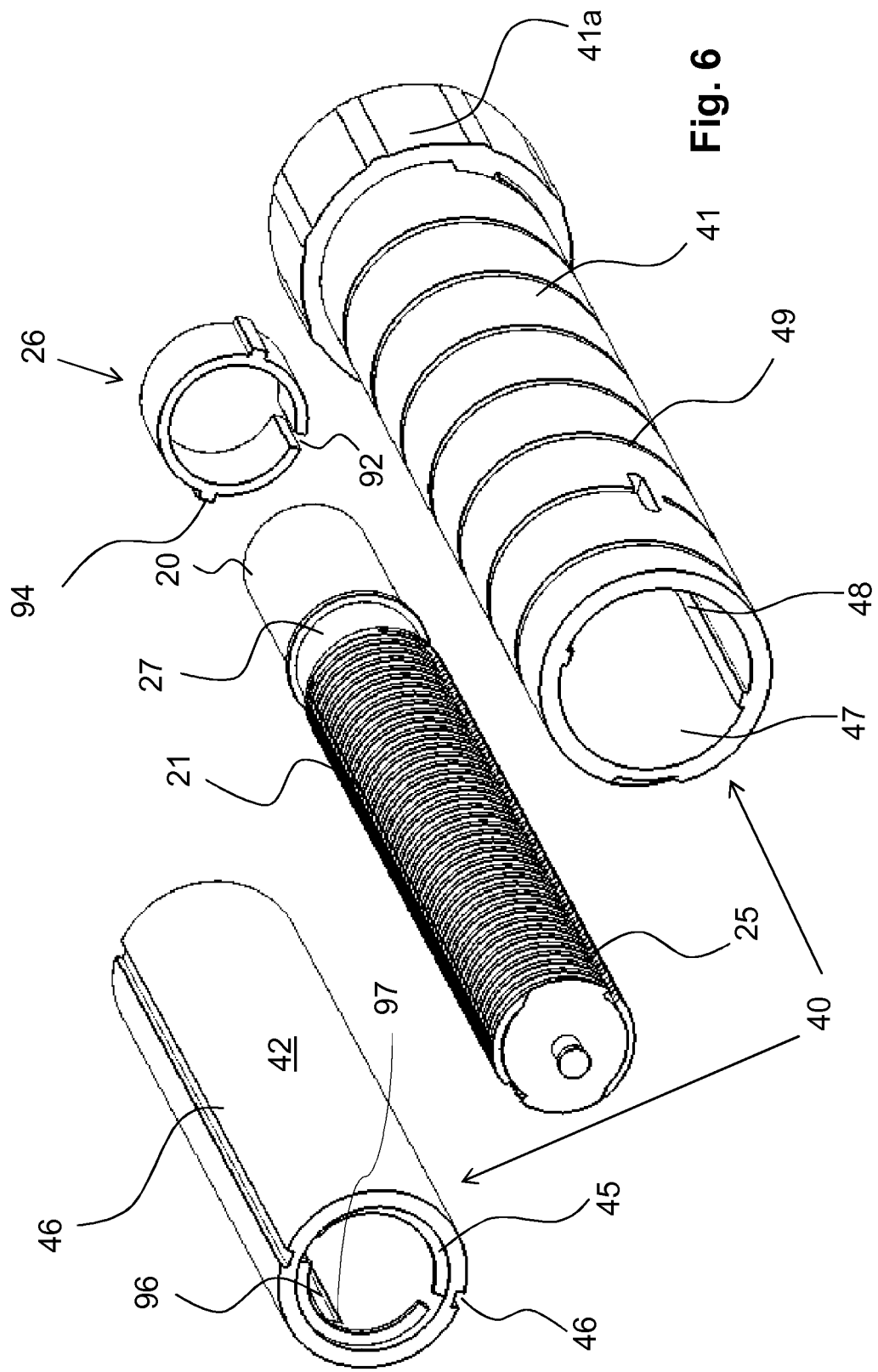
FIG. 6 shows a partly exploded view of the medicament delivery device according to FIG. 1.

Outside the piston plunger 20 as seen in a radial direction, a telescopic dose (setting) drum 40 is arranged (FIGS. 5 and 6). The dose drum 40 has a generally tubular shape and is positioned coaxial with the piston plunger 20 as well as the housing 10. The dose drum 40 comprises a first, distal, part 41 and a second, proximal, part 42 being slidably arranged relative to each other. The distal part 41 is located coaxially radially outside of the proximal part 42 of the dose drum 40.

The distal part 41 comprises a helically or spirally extending groove 49 (FIG. 6) on its outer side surface 41. The groove 49 extends all the way from the proximal end to the distal end of the distal part 41 of the dose drum 40. The groove 49 is intended to cooperate with at least one protrusion or spirally extending ledge segment 16 (FIG. 5) arranged on the inner surface of the housing 10 such that the dose drum 40 is rotationally connected to the housing 10, whereby mutual rotation causes movement in the longitudinal direction of the parts. The distal end area of the first part 41 of the dose drum 40 is further arranged with a locking structure that engages with the locking structure 36 of the drive drum sleeve 30 when the drive drum sleeve 30 is moved into the piston plunger 20 during assembly of the medicament delivery device.

At the distal end of the first part 41 the dose setting knob 41a is arranged (FIG. 6). The dose setting knob 41a comprises a proximally directed generally tubular part having a diameter somewhat larger than the outer surface of the first part 41 of the dose drum 40. The outermost diameter of the dose setting knob 41a is preferably flush with the outer diameter of the housing 10. The first part 41 of the telescopic dose drum 40 is thus configured to rotationally move distally in the first direction relative to the housing 10 during dose setting by the dose setting knob 41a.

The inner circumferential surface 44 of the second part 42 of the telescopic dose drum 40 is threadedly connected to the threaded outer circumferential surface 21 of the piston plunger 20. In particular, the proximal end of the second part 42 comprises a threaded structure 45 (FIG. 6). The threaded connection between the first part 41 of the telescopic dose drum 40 and the inner circumferential surface of the housing 10 has a pitch different to the pitch of the threaded connection of the inner circumferential surface 44 of the second part 42 of the telescopic dose drum 40 and the threaded outer circumferential surface 21 of the piston plunger 20.

According to the invention the device further comprises a stop body 26 being connected to the hollow piston plunger 20 such that said stop member is rotatable but not slidable in relation to said hollow piston plunger 20, and being also connected to the telescopic dose drum such that said stop member is slidable but not rotatable in relation to said telescopic dose. Said stop body 26 is configured to interact with a stop member 97 on said telescopic dose drum 40 when the set dose equals the remaining dose in the medicament container such that rotation of the telescopic dose drum 40 is inhibited. The stop body 26 is a generally ring-shaped body (FIG. 6) comprising at least one protrusion, rib or ledge 94 on its outer surface. Further, the second, proximal, part 42, which is a tube shaped body, comprises at least one longitudinally extending groove 96 on in its inner surface and wherein said stop member 97 is an end surface of said at least one groove. The stop body is arranged to fit in a circumferential groove 90 on the piston plunger, where the groove is arranged at the distal end area of the threads 21 on the outer surface of the piston plunger 20. In order to fit the ring-shaped body in the groove of the piston plunger, the stop body is arranged with a slit 92 and being made of an elastic material, thereby enabling the widening of the gap of the slit 92 such that the body 26 may be pushed onto the piston plunger. When in place, the body 26 is rotatable in relation to the piston plunger, but locked in the longitudinal direction. The rib(s) 94 of the stop body 26 is/are intended to fit into the longitudinally extending grooves 96 (FIG. 6) arranged on the inner circumferential surface 44 of the second part 42, whereby the stop body 26 is rotatably locked to the second part 42, but slidable in the longitudinal direction relative the second part 42.

Figure 9:
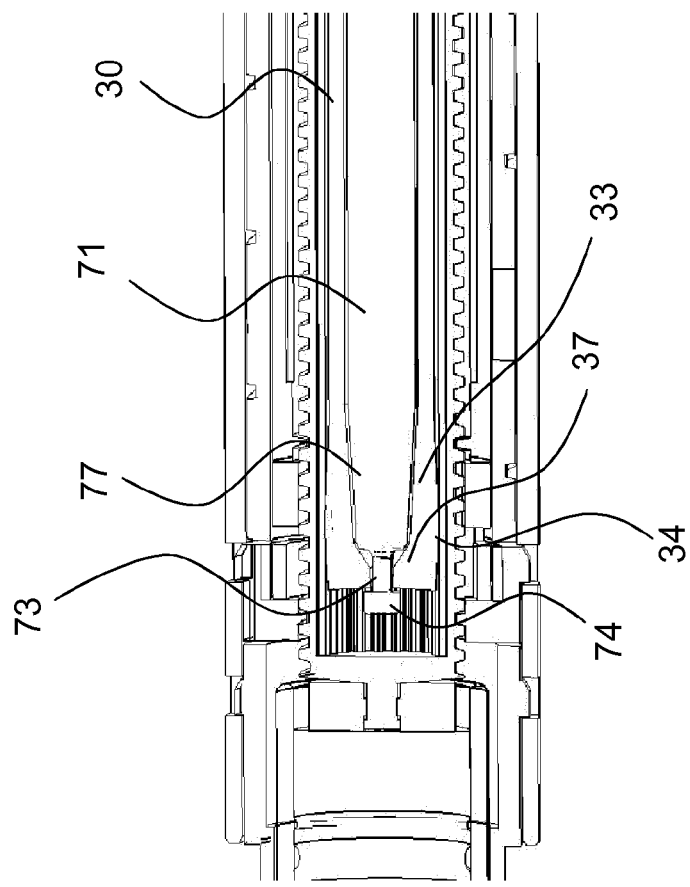
FIG. 9 shows a detailed cross-sectional view taken from marked area IX of FIG. 8.

The resilient spinning element 70 comprises a longitudinal rod 71 and a distal push button 72. The push button is intended to act as a contact surface for a finger of a user during drug delivery, as will be described. As described above, the longitudinal rod 71 of the resilient spinning element 70 is accommodated within the hollow drive drum sleeve 30. At its proximal end, the longitudinal rod 71 comprises an engagement structure comprising a circumferential groove 73 (FIG. 9). Adjacent the groove and in the proximal direction is a protrusion 74 and in the distal direction an inclined surface 77. The size of the groove 73 and the location on the longitudinal rod 71 is such that the radially inwardly directed protrusion 37 on the flexible arms 33 of the drive drum sleeve 30 is initially received in the groove 73. In such initial stage, the flexible arms 33 are not deflected radially outwards but are in a tension-free state.

Figure 10:
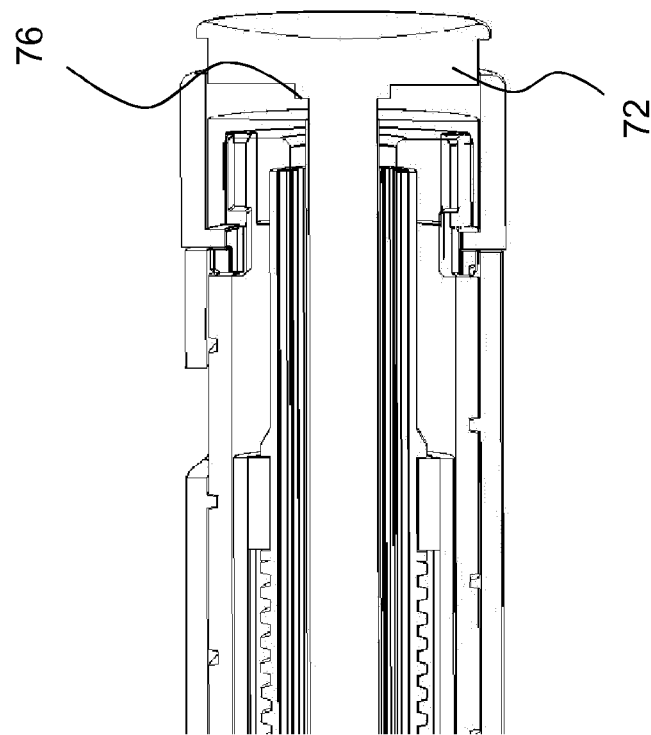
FIG. 10 shows a detailed cross-sectional view taken from the marked area X of FIG. 9.

The axial length of the resilient spinning element 70 in comparison to the drive drum sleeve 30 is such that in the initial state of the medicament delivery device, i.e. with the engagement protrusion 37 being received in the groove 73, the proximal surface of the push button 72 is spaced from the distal surface of the coupling element 31 by a gap 76 (see, e.g., FIG. 10). This gap 76 is maintained when a dose is set by a user and the first part 41 of the dose drum 40, the drive drum sleeve 30 and the resilient spinning element 70 are moved distally. However, as soon as the push button 72 is pushed towards the proximal direction, the push button 72 first bridges the gap 76 thereby moving the longitudinal rod 71 in proximal direction relative to the drive drum sleeve 30. Due to such relative displacement, the inclined surface 77 is moved in contact with, and is pressed against, the engagement protrusion 37 on the flexible arms 33, thus deflecting the arms 33 outwardly and into engagement with the longitudinal splines on the inner surface 22 of the piston plunger 20.

Description of the Function and Operation of the Embodiment

Setting Operation for a Dose to be Delivered

Figure 8:
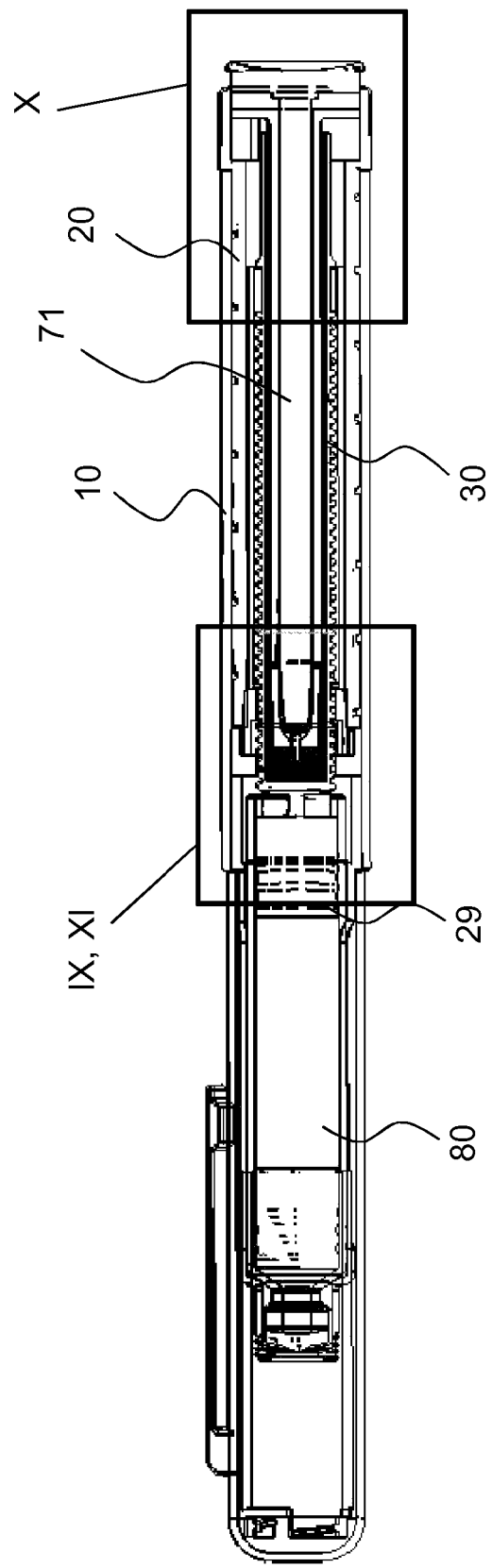
FIG. 8 shows a cross-sectional view of the medicament delivery device according to FIG. 1, shown in the initial state.

FIG. 8 shows a cross-sectional view of the medicament delivery device in the initial state.

In order for a dose to be delivered, the device must be operated to set a dose. In order to set a dose to be delivered the user grips the housing 10 and the distally arranged dose setting knob 41a and turns them in relation to each other, where the dose setting knob 41a is turned in the clockwise direction, for example. The turning of the dose setting knob 41a will cause the first part 41 of the dose drum 40 to be rotated. The connection between the helical groove 49 of the dose drum 40 and the spiral ledge segment of the housing 10, the rotation will cause the first part 41 of the dose drum 40 to move in the distal direction in relation to the housing 10. Inside the dose setting drum 40 the drive drum sleeve 30 will also rotate because of the rotational lock both at the distal end 31 of the drive drum sleeve 30 with the dose drum 40. Thus the drive drum sleeve 30 is rotationally connected to the dose drum 40.

The longitudinal ribs 48 on the inner surface of the first part 41 of the dose drum 40 are in contact with the longitudinal grooves on the outer surface of the second part 42 of the dose drum 40. Thus, the first part can slide relative to the second part. Furthermore, the second part 42 is also rotated and due to the threads 45 engaging into the threaded surface of the piston plunger 20, the second part 42 also moves distally, albeit at a lower speed than the first part 41 due to the different pitches. Rotation of the second part 42 also causes a certain turning force on the piston plunger 20, which also urges the back rotating blocking element 60 to turn due to the rotational lock between the blocking element 60 and the piston plunger 20 because of the protrusions 66 of the back rotating blocking element 60 fitting into the longitudinal grooves 25 of the piston plunger 24. However, the arms 62 of the back rotating blocking element 60 are directed such and cooperating such with the ratchet 55 of the thread insert 50 that any rotation of the back rotating blocking element 60 is prevented. Thus the piston plunger 20 is prevented from rotating. During rotation, preferably indicia (not shown) on the dose drum 40 are shown through the window or opening 13 at the distal end 12 of the housing 10. The patient thus rotates the dose setting knob 41a until the prescribed dose quantity is displayed.

If the user by mistake has set a too large dose, he/she simply turns the dose setting knob 41a in the opposite direction, whereby both the dose drum 40 and the drive drum sleeve 30 are turned in the opposite direction until the correct dose has been reached.

FIG. 10 shows a cross-sectional view of the medicament delivery device in the state when a dose is set. In particular, it can be seen that the gap 76 still exists.

Delivery Operation of a Pre-Set Dose of Medicament

In order to deliver a dose of medicament, the user presses the proximal end of the device against a dose delivery site, and in particular an injection site when the medicament delivery member is an injection needle. The next step is to press on the activator button 72 at the distal end of the device. This causes the gap 76 to close due to the force applied by the user and the button 72 contacts the distal coupling member 31 of the drive drum sleeve 30.

The force on the activator button 72 will first bring the drive drum sleeve 30 into engagement with the inner surface of the piston plunger 20, as already described above. Secondly, once the gap 76 has been bridged, the force on the activator button 72 urges the dose activator knob 41a in the proximal direction. This proximal force will be transferred to the dose drum 40 and due to the threaded connection with the housing 10, the dose setting drum 40 will rotate, now in the anti-clockwise direction, and move in the proximal direction. Because of the rotational lock between the dose drum 40 and the drive drum sleeve 30, the latter will also rotate. Due to the radial flexing of the arms 33 of the drive drum sleeve 30, the radially outwardly directed surface 34 of the drive drum sleeve 30 firmly engage the splines 23 of the piston plunger 20.

Thus when now the dose drum 40 and the drive drum sleeve 30 rotate, the latter will urge the piston plunger 20 to rotate as well. This rotation in the anti-clockwise direction will be allowed by the back rotating blocking element 60 due to the design of its arms 62 in contact with the ratchet 55 of the thread insert 50. The piston plunger 20 will thus rotate together with the back rotating blocking element 60, and the arms 62 of the back rotating blocking element 60 sliding over the ratchet 55 of the thread insert 50 will provide audible and tactile information. Further the rotation of the piston plunger 20 will cause it to be moved in the proximal direction due to the threaded connection with the thread insert 50, whereby the movement of the piston plunger 20 will urge the stopper 29 in the proximal direction, thereby expelling a dose of medicament through the dose delivery member. The dose has been delivered when the dose drum 40 has moved back to its initial position, which could be limited by some sort of blocking member (not shown) preventing further movement or rotation of the dose drum.

The device may now be removed from the dose delivery site, and the medicament delivery member discarded. If the medicament container 85 still contains a large enough dose to be delivered, the above steps may be repeated from the step "Setting operation for a dose to be delivered".

Figure 11:
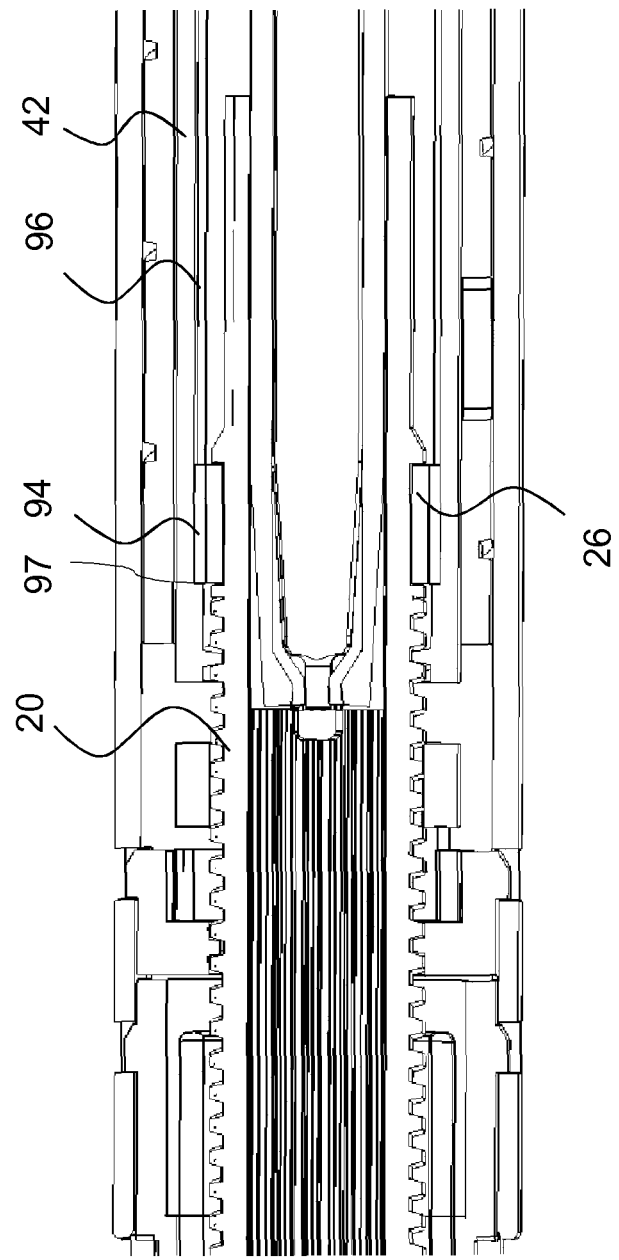
FIG. 11 shows a detailed cross-sectional view taken from the marked area XI of FIG. 9.

If the medicament container however contains a dose that is smaller than the prescribed dose, the present invention prevents setting a dose that is larger than the remaining dose. When the dose setting knob 41a is rotated as described above the second part 42 of the dose setting sleeve is also rotated in relation to the piston plunger 20 and due to the threaded connection between the second part 42 and the piston plunger 20, the second part 42 is moved in the distal direction. The ribs 94 of the stop body 26 will slide in the grooves 96 of the second part 42 during rotation, but when the maximum dose is set, the ridges 94 will come in contact with the end surface of the groove 96 (FIG. 11), which is the stop member 97, thereby preventing any further setting of a dose. Thus, the stop body 26 prevents any further turning of the dose setting knob 41a, thereby preventing setting a dose that is larger than the remaining dose.

Preferably the device is arranged with some indicia or other information means that indicates the quantity of the last, inferior, dose so that the user may take a subsequent complementary dose with the missing volume. In this manner, also all medicament is used in the medicament container, whereby no medicament will go to waste because the remaining dose is smaller than the prescribed.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device, comprising:
   a housing having a proximal end and a distal end;
   a hollow piston plunger within the housing;
   a telescopic dose drum concentrically arranged between the housing and the piston plunger, the dose drum being bidirectional movable in relation to the housing and in relation to the piston plunger when setting a dose and delivering a dose;
   a piston plunger driver configured to drive the piston plunger toward the proximal end, comprising:
      a hollow drive drum sleeve movably arranged within the piston plunger and fixedly connected to the dose drum, wherein the drive drum sleeve and piston plunger are releasably coupled to each other;
      a resilient spinning element having a longitudinal rod movably arranged within the drive drum sleeve, wherein the rod and drive drum sleeve are releasably coupleable to each other such that after a dose is set, axial movement of the resilient spinning element toward the proximal end forces the rod and drive drum sleeve to couple and thereby the drive drum sleeve and piston plunger to couple, whereby the piston plunger and dose drum are displaced toward the proximal end for delivering the set dose, and such that after the set dose is delivered, axial movement of the resilient spinning element toward the distal end forces the rod and drive drum sleeve to uncouple and thereby the drive drum sleeve and piston plunger to uncouple for setting a new dose;

a stop body connected to the piston plunger such that the stop body is rotatable but not slidable in relation to the piston plunger; and a stop member connected to the dose drum, wherein the stop member and stop body are configured to interact when the set dose equals a remaining dose in a medicament container such that rotation of the dose drum is inhibited.

2. The medicament delivery device of claim 1, wherein the stop body is ring-shaped having at least one protrusion, rib, or ledge on its outer surface.

3. The medicament delivery device of claim 1, wherein the stop body is ring-shaped having at least one protrusion, rib, or ledge on its outer surface.

4. The medicament delivery device of claim 1, wherein the dose drum includes a first distal part and a second proximal part, the parts being slidable relative to each other.

5. The medicament delivery device of claim 4, wherein the second proximal part is a tube-shaped body comprising at least one longitudinally extending groove on in its inner surface, and the stop member is an end surface of the at least one groove.

6. The medicament delivery device of claim 4, wherein the first distal part comprises at its distal end a dose setting knob configured to be grasped by a user for setting a dose when being rotated in a first direction.

7. The medicament delivery device of claim 6, wherein the dose setting knob is connected with a first part of the dose drum at its distal end, whereby the first part of the dose drum is configured to move rotationally and distally in the first direction relative to the housing during dose setting by the dose setting knob.

8. The medicament delivery device of claim 1, further comprising a medicament container holder configured to receive a medicament container.

9. The medicament delivery device of claim 1, wherein part of an outer circumferential surface of the piston plunger is threaded.

10. The medicament delivery device of claim 1, further comprising a unidirectional device configured to prevent movement of the piston plunger in a distal direction during setting a dose.

11. The medicament delivery device of claim 1, wherein the medicament deliver device is an injection device.

12. The medicament device of claim 11, wherein the injection device is a pen injector.

* * * * *